(12) United States Patent
Weiss

(10) Patent No.: US 6,471,715 B1
(45) Date of Patent: Oct. 29, 2002

(54) SUTURE TIGHTENING DEVICE FOR CLOSING WOUNDS AND METHOD FOR ITS USE

(75) Inventor: Jerry Weiss, Hertzelia (IL)

(73) Assignee: Wisebands Ltd, Ofakim (IL)

( * ) Notice: Subject to any disclaimer, the term of this patent is extended or adjusted under 35 U.S.C. 154(b) by 0 days.

(21) Appl. No.: 09/601,383

(22) PCT Filed: Jan. 18, 1999

(86) PCT No.: PCT/IL99/00031

§ 371 (c)(1),
(2), (4) Date: Jul. 21, 2001

(87) PCT Pub. No.: WO99/35974

PCT Pub. Date: Jul. 22, 1999

(30) Foreign Application Priority Data

Jan. 19, 1998 (IL) ................................................ 122994

(51) Int. Cl.[7] .............................................. A61B 17/04
(52) U.S. Cl. ....................... 606/216; 606/217; 606/218; 606/233
(58) Field of Search ................................ 606/216, 217, 606/218, 233

(56) References Cited

U.S. PATENT DOCUMENTS

| | | | |
|---|---|---|---|
| 3,650,274 A | * | 3/1972 | Edwards et al. ............. 606/233 |
| 3,910,281 A | | 10/1975 | Kletschka |
| 3,931,821 A | * | 1/1976 | Kletschka et al. .......... 606/233 |
| 5,127,412 A | | 7/1992 | Cosmetto |
| 5,330,489 A | | 7/1994 | Green |
| 5,356,412 A | | 10/1994 | Golds |
| 5,364,407 A | | 11/1994 | Poll |
| 5,462,542 A | | 10/1995 | Alesi |
| 6,050,937 A | * | 4/2000 | Benderev ...................... 600/37 |

FOREIGN PATENT DOCUMENTS

IL                 097225            2/1991

OTHER PUBLICATIONS

Gibson & Kenedi, Biochemical properties of skin, Surg Clin North Am, 1967, 47: 279–94.
A.H. Bashir, Wound Closure by skin traction, British Journal of Plastic Surgery, 1987, 40:582–587.
Bernard H. Cohen and A. John Cosmetto, The Suture Tension Reel adjustment, Dermatol Surg Oncol, 1992, 18:112–123.

* cited by examiner

Primary Examiner—Gary Jackson
(74) Attorney, Agent, or Firm—Lilling & Lilling P.C.

(57) ABSTRACT

The present invention relates to a suture tightening wound closure device for use on mammals including humans. This device is comprising a smooth suture (to be sewn across an open wound through the skin and underlying tissue) and a suture loop tension means (for closing the wound). This tension means is by grasping one end of the suture, and pulling back its second end, forming a tensioned suture loop, enclosing the wound. Specifically, the device of the present invention is characterized by the tension means having a manual control mechanism (for pulling or releasing said second end). The smooth suture according to the preferred embodiment of the present invention is a suture band, which is flexible for bending along it's length and is resistant to bending along it's width. The device of the present invention also relates to embodiments having in addition a pair of suture supporting skin reinforcing means.

21 Claims, 11 Drawing Sheets

SUTURE TIGHTENING DEVICE FOR CLOSING WOUNDS AND METHOD FOR ITS USE

FIELD OF THE INVENTION

The present invention relates to a suture tightening wound closure device and to a method for its use. In particular the device of the present invention is comprised of a suture and a suture loop tension means (for providing a controlled tension to the applied suture). The present invention also relates to method for closing open wounds using the device of the present invention. The suture is looped through the skin and underlying tissue around large open wounds, and tightened gradually (using the suture loop tension means) to bring the wound edges into proper alignment.

BACKGROUND OF THE INVENTION

Skin is a visco-elastic tissue that can be stretched by mechanical creep and by biological creep. Mechanical creep occurs when a constant load applied to the skin causes increasing amount of skin extension over time. Stress relaxation is another aspect of the mechanical creep that occurs when the force required to maintain skin stretched decreases over time. Gibson and Kenedi (Gibson T, Kennedi Rm.Biomechanical properties Surg Clin North Am 1967;47:279–94) have noted that skin can be stretched to four times its original length provided that the force applied is limited, and does not cause blanching or breakage of the collagen fibers in the dermis. Biological creep is the slow expansion of the tissue, accompanied with the generation of new collagen and elastic epithelium fibers.

In the case of large skin and tissue deficits (caused by trauma or by surgical resection), the skin and soft tissue defect cannot usually be closed by conventional suturing. Over the years some techniques have been developed to address the problem. The conventional surgical technique involves skin grafts and skin flaps which require skin elevation and removal from another part of the body. This technique is invasive, requires special hospitalization, and costs substantially.

Other techniques harness the visco-elastic properties of skin. The most known technique "Tissue Expansion" is based on the biological creep effect. The expander is implanted under the skin and inflated slowly to expand the skin. This procedure is also expensive and requires a second surgical procedure to transfer expanded skin to the wound area.

More recent techniques and devices are based on the mechanical creep effect of the skin. Hirshowitz et al. (Israel Patent No.097225) developed a skin stretching device that consists of two "U" shaped arms with sharp cutting hooks that engage two long pins that are threaded through the dermis on either side of the wound. The arms can then be pulled closer to each other and stretch the skin by a screw turned by a tension knob. Bashir (British Journal of Plastic Surgery 1987,40,582–587-Wound Closure By Skin Traction) applied the mechanical creep effect by threading steel wires through the edges of the defect and then over a period of days twisted them to apply tension to the skin. Cohen et al. discloses a Suture Tension Adjustment Reel that is applied to gradually tighten a suture that is passed through the two opposing skin edges of the wound (Dermatol Surg Oncol 1992;18:112–123 and U.S. Pat. No. 5,127,412).

The existing methods and devices that are based on the mechanical creep of the skin suffer from some shortcomings. They are bulky, restrict patient's movement, and hard to bandage over. Further, the tension is applied to the external surface of the skin without effectively affecting the underlying tissue. This is not sufficient when the tissue deficit is large and deep. The closure that will be achieved might be partial, leaving dead space under the skin in which contamination can occur. Also some of those technique require that sutures will be applied once the skin edges are close enough to withstand the tension exerted by the suture. The patient has to be left then in the operating room until the skin edges are brought together, or alternatively if the stretching procedure takes time he is transferred to a recovery room and returned later to the operating room.

Recently, some new methods have been developed for sternum repair based on using a band assembly (with a needle) secured by a buckle mechanism in a closed loop configuration about the sternum portions. Typical assemblies are described in U.S. Pat. Nos. 5,462,542, 5,330,489, 5,356,412 and more.

The devices described by the above mentioned patents could not be used effectively for large wound closure. In most of the methods the strap is not smooth enough for skin application, and therefore new tissue can grow into the strap during the period in which it is implanted in the body. Further, the buckle mechanism in some of the applications is usually designed to lock the band in one secure position, whereas for wound closure application a delicate and controlled movement exercised by the mechanism is required. Additionally, those devices are not provided with any means to indicate the tension applied to the skin.

Thus, there is a clear need for a wound closure (surgical) device and method which is simple in construction and application, permitting delicate and controlled wound edges and underlying tissue stretching by high-surface-area suture (or ordinary suture), and finally small and non obstructive.

The preferred embodiment of the device of the present invention is directed to a suture tightening wound closure device (a stretching mechanism assembly) including a base (suture tensioning means), a suture, a surgical needle, a specialized skin reinforcing staple, and a suture loop tension measuring and displaying means.

The method of the present invention is directed to using this suture tightening wound closure device by gradually applying a safe controlled tension to the in place suture, with intervals for skin stress self relaxation.

SUMMARY OF THE INVENTION

The present invention relates to a suture tightening wound closure device for use on mammals including humans. This device is comprising a smooth suture (to be sewn across an open wound through the skin and underlying tissue) and a suture loop tension means (for closing the wound). This tension means is by grasping one end of the suture, and pulling back its second end, forming a tensioned suture loop, enclosing the wound. In the context of the present invention, "one end" or "the first end" of the suture, relates to that end of the suture which is immovably fixed in the device as a beginning of the suture loop; "the second end" of the suture, relates to that portion of the suture which is variably controlled and driven by the suture tension means. Specifically, the device of the present invention is characterized by the tension means having a manual control mechanism (for pulling or releasing said second end).

Preferred embodiments of the device of the present invention have in addition a means for measuring and displaying the tension in the suture loop.

The smooth suture according to the preferred embodiment of the present invention is a suture band, which is flexible for bending along it's length and is resistant to bending along it's width.

Furthermore, the device of the present invention also relates to embodiments having in addition a pair of suture supporting skin reinforcing means (for preventing ripping of the skin when tension is applied to the suture loop). Each of these reinforcing means is comprised of a rigid plate (for placing on the skin near a suture's skin piercing point) and a means for preventing each plate from slipping. According to various embodiments of this skin reinforcing means, the suture passes over or passes through the plate. Embodiments of the means for preventing slipping according to the present invention include skin piercing stickers, adhesives, and the like.

The present invention also relates to a method for the closing of open wounds using of the suture tightening device of the present invention.

DETAILED DESCRIPTION OF THE INVENTION

The present invention relates to a suture tightening wound closure device (for use on mammals including humans), comprising a smooth suture (to be sewn across an open wound through the skin and underlying tissue) and a suture loop tension means (for closing the wound by grasping the first end of the suture and pulling back the second end of the suture). This suture tightening wound closure device is characterized by the tension means having a manual control mechanism (for pulling or releasing said second end).

According to one embodiment of the present invention, the first end of the suture is integrally attached to the suture loop tension means.

In the preferred embodiment of the suture tightening wound closure device of the present invention, there is in addition a means for measuring and displaying the tension in the suture loop. This means for measuring and displaying the tension in the suture loop may be a tension meter (such as a torque meter, a dynamometer (base or rotary), a lever gage, or a tensio-meter). It is preferred (by reasons of the surgeon's convenience) that the means for measuring and displaying tension in the suture loop is integrally attached to the suture loop tension means (or otherwise incorporated therein).

Furthermore, the tension means may additionally be characterized by automatically relieving any excess suture tension (by releasing suture back into the suture loop). This feature may not be specifically necessary when the device of the present invention is used with a method that monitors the suture loop tension (so as never to exceed the safe tension level).

In the context of the present invention, "suture" relates to any standard surgical tissue sewing fiber. Furthermore, the term "suture band" in the context of the present invention may be comprised of non-absorbable synthetic fibers or from bio-absorbable fibers. For additional convenience the suture (or suture band) head end preferably has an integrally attached surgical needle. Likewise the suture (or suture band) tail end preferably has a cross section enlargement or a clip (for facile grasp by the tension means).

According to the preferred embodiment of the present invention the smooth suture is a suture band, which is flexible for bending along the band's length where simultaneously the band is resistant to bending along it's width. For example a flat band suture material should be smooth and impregnable, with resistance to twisting and buckling higher than that of it's resistance to bending. Thus according to the present invention, a "smooth" suture band need only have a low friction profile length-wise (in the tissue sewn sewing direction). The cross-section of the suture band may be convoluted to enhance its asymmetric bending resistance properties. These convolutions may create a high friction profile when the suture band is viewed in cross-section, but this does not interfere with the "smoothness" of the suture band as required for sewing through skin and tissue (without causing additional abrasions).

The device of the present invention is best used with a method of spreading (over a wider area of skin) the stress made by the tension of the suture. One simple solution is the using of a hook anchored to the skin (or tissue) with the suture passing through the hook (so that some or all of the tension force is taken by the hook rather than by the immediate tissue surrounding the suture). For purposes of the present invention, hooks and functionally equivalent peripheral devices are referred to as suture supporting skin reinforcing means, or simply as reinforcing means.

The preferred embodiment of the present invention has in addition a pair of suture supporting skin reinforcing means for preventing ripping of the skin when tension is applied to the suture loop. Each of the reinforcing means is comprised of a rigid plate for placing on the skin near a suture's skin piercing point (wherein the suture passes over or passes through the plate) and a means for preventing the plate from slipping.

The preferred embodiment of the reinforcing means is a staple, having a broad back for supporting the suture, and having integral skin piercing stickers at both ends for preventing slippage. According to other embodiments, the reinforcing means is a plate having a broad back (for supporting the suture), and having integral skin piercing stickers at predetermined locations (along the skin facing side of the back) for preventing slippage. According to another significant embodiment of the present invention, the means for preventing the plate from slipping is by use of adhesive (between the plate of the reinforcing means and the skin surface).

According to the preferred embodiment of the suture tightening wound closure device, a reinforcing means is integrally affixed to the wound facing side of the tension means (for placement against the skin at the suture entry point or at the suture exit point).

In the preferred embodiments of the present invention the manual control mechanism of the suture loop tension means is operated by a rotating component. The rotating component may be a lead screw, a rack, or a drum. The controlled pulling or controlled releasing on a suture may be performed by turning the rotating component clockwise or counterclockwise (for example by using an attached knob). According to certain embodiments of the present invention, there is in addition the option of actuating the tension means by the manual pulling on second end of the suture.

In an embodiment of the present invention, the suture loop tension means is comprised of a suture ends holder assembly (buckle). This assembly has two openings (for passing respective suture ends through). A clip is located at one of the openings (for grasping the first end of the suture). A ratcheted drum (one way clutch rack) is located above the other opening (for applying wound closing tension through the attached or passing second end of the suture). Additionally there is a means for manually turning the drum (such as a twistable knob, a trigger, etc.).

This "ratcheted drum" suture loop tension means is for maintaining a one-way tension on suture material using geometric locking. Accordingly, the friction force keeping the suture tight is increased proportionally to any increase in the force of tension in the suture material, while simultaneously pull to the other direction can increase the tension in the suture loop without overdue resistance. By spooling the suture onto the rack (or drum), the rack (or drum) is prevented by the ratchet (or one-way clutch) from rotating back under the moment force of the tension. Another alternative "ratchet drum" suture loop tensioning means is presented in the accompanying illustrated figures.

According to the preferred embodiment of the suture loop tensioning means, the band may be pulled by friction with a rotating shaft (the shaft prevented from counter rotation by means of a ratchet or one-way clutch). Additionally the suture loop tensioning means may be incorporating a press lever for amplification of the friction force proportionally to any increase in the tension in the band.

According to a preferred embodiment of the "ratchet drum" suture loop tension means, a spring is located in the holder and pressing on the ratchet end of the drum's axle (for releasing the ratchet teeth from their counter locking tooth whenever the suture loop tension is exceeding the predetermined tension). This is as an additional safety feature to disengage the locking as long as the tension on the suture is above the set safety limit. The disengagement may be either by a mechanism for controlled release of suture from the rack (or drum) without loss of tension or by a mechanism for releasing the drum or rack for complete tension removal. An alternative preferred embodiment additionally incorporates a safety feature to disallow tensioning over a set safe limit (rather than additionally incorporating a safety feature to release tension exceeding a set limit).

In a second preferred embodiment of the present invention, the suture loop tension means is comprised of a suture ends holder assembly having two openings for passing respective suture ends through, wherein a clip is located at one of the openings (for grasping the first end of the suture), a reversible lead screw is located above the other opening (for applying or releasing wound closing tension through the passing second end of the suture), and means for manually turning the screw is provided (such as a twistable knob, a trigger, etc.).

This "lead screw" suture loop tension means is for maintaining a one-way tension on suture material. According to the preferred embodiment of the "lead screw" embodiment, in addition the holder facing end of the screw is ball profiled, and a ball joint socket with an elongated opening located in the holder holds the ball end of the screw. This ball and socket is for allowing the angle of the screw in the holder to be manually switched to either an open position (for the complete release of applied tension to the suture loop), or to a closed position (for the complete prevention of any release of excess tension in the suture loop). According to another "lead screw" embodiment, the lead screw may be lifted from the working position in the holder (to enable the band insertion, slack pull, or complete release of tension on the band).

The device embodiments of the present are most easily understood when viewed in conjunction with the method for their use. The suture tightening wound closure device and the method of the present invention are based upon the visco-elastic properties of skin in which large open wounds can be brought into closure by applying incremental and controlled tension. The general embodiment of our device includes a tension-buckle assembly, and a flexible suture (with a surgical needle connected). The tension-buckle mechanism is placed on one side of the wound and the suture is looped through either the skin, or through both the skin and underlying tissues. The suture is tightened periodically by the mechanism within tolerable levels and then left secure by said mechanism while tension drops (due to tissue self relaxation) allowing for repeated tightening.

The general method of the present invention pertains to closure of large skin and soft tissue deficits caused by trauma or surgical procedure. Such wounds are difficult to close by regular suture and currently require either a prolonged process of re-suturing and secondary healing, or other surgical procedures (such as by skin grafts, or by skin flaps).

Thus, the general preferred embodiment of the present invention is directed to a wound closure stretching device which includes a base member tension-buckle mechanism, a suture, a surgical needle, a specialized staple, and a suture loop tension measuring and display means. The recommended suture is a wide area smooth surfaced monofilament band. The band is preferably inserted through the entire depth of soft tissue to be tightened together, with the wide sides toward the line of tensioning, and the end of the band protruding out. The puncture points through which the band end exits can be reinforced by any method of pressure distribution, so as to not lacerate the skin or upper tissue layer. The suture is looped around the open wound edges and then locked into the base mechanism (which has the capability to stretch the suture or to loosen it gently when needed). Additional feature includes visual indication of the tension existing in the suture.

The method according to the present invention for closing open wounds using the suture tightening wound closure device as defined in this invention, is comprised of;
(A) Sewing a smooth suture across an open wound through the skin and underlying tissue.
(B) Affixing the suture ends in the tension means.
(C) Gradually applying a predetermined tension to the suture loop with intervals for skin stress self relaxation until the wound edges are brought into proper alignment, or until the wound is otherwise sufficiently closed, or for delayed primary closure of said wound.

This method for wound closure uses free-sliding suture to pull the wound lips together in a cycled tensioning (with tension measured) applied to a safe load and then left to diminish to a lower level by self relaxation of the tissue. The process then repeated until the wound is sufficiently closed.

Accordingly it is methodologically preferred that;
(A) The predetermined tension is not exceeding a safe level as measured by the tension meter.
(B) In addition, after the suture is sewn across the open wound and before the suture ends are attached to the tension means, a pair of reinforcing means is applied (one on each of the skin covered sides of the wound).
(C) Parallel sutures are sewn across an open wound, and tension means is applied to each suture independently (in cases where the wound demands multiple sutures).
(D) Supporting more than one suture by a pair of reinforcing means is elected according to convenience.

According to various embodiments of the device of the present invention, the method for use thereof may in addition require;
(A) After the suture is sewn across the open wound, removing the needle from the suture.
(B) After the wound edges are brought into the desired alignment, allowing a predetermined time for the skin stress self relaxation, removing the tension means, and the tying together or otherwise making fast of the suture ends.

(C) After the wound edges are brought into the desired alignment, using the tension means as a suture locking buckle.

(D) Opening the suture buckle allowing access to internal wound tissues for supplemental treatment.

(E) Reapplying the tension means to an in place suture, and gradually bringing the wound edges into the desired alignment therewith.

The present invention is also directed as a method of closing large skin defects, and may alternately be according to one of the following methodological scenarios;

(A) Inserting the suture through the skin and the underlying soft tissue layers on one side of the wound and looping it around the open wound into the base mechanism. Further tightening the suture gently to create limited tension on the skin (avoiding any blanching of skin). Using visual indication of tension to keep the tension under low levels. Applying additional tightening when tension is zeroed due to stress relaxation. Repeating the procedure until the wound edges are completely aligned. Leaving the device on the patient's body until complete healing of the wound is achieved. For large and long wounds several devices in a row may be used concurrently at a distance of 2–4 centimeters from one another.

(B) Applying of the device in cases of trauma injuries where delayed primary closure is required. Inserting sewing suture into the tissue, looping the suture around the wound, and securing the base mechanism without applying any tension force. When the edema in tissues is decreased, then tightening the suture gradually in a similar way to the procedure mentioned above.

The present invention will be further described by FIGS. 1–10. These figures are solely intended to illustrate the preferred embodiments of the invention and are not intended to limit the scope of the invention in any manner.

FIG. 1 illustrates a cutaway side view through a section of tissue in which the preferred embodiment of the method under this invention is presented.

FIG. 2 relate to the relative stress concentration and tear mode for a circular pin or thread (FIG. 2A), a flat band (FIG. 2B), and a flexible band which is buckling under tension (FIG. 2C).

FIG. 3 illustrates two perspective views showing a flat mono-filament suture band.

FIG. 4 relate to a lead screw embodiment suture tightening device. FIG. 4A illustrates an exploded isometric view of a suture tightening device. FIG. 4B illustrates a cutaway side view through the suture tightening device (shown in FIG. 4A) for applying, measuring, and retaining of tension. In FIG. 4C, the means for measuring and displaying tension in the suture loop is shown from above.

FIG. 5 relate to an alternative embodiment of a "ratchet drum" manual control mechanism for applying or releasing tension through the attached or passing head end of a suture, wherein a tension measuring and displaying means has been incorporated. FIG. 5A illustrates a perspective exploded view of the ratchet drum device for applying, measuring, and retaining of tension, with the incorporated tension measuring means. FIG. 5B illustrates a suture end attached to a ratchet drum. FIG. 5C illustrates a ratchet drum with a passing head end of a suture.

FIG. 6 relate to another alternative tensioning device. This is part of a non-ratcheted drum embodiment of the present invention. Also integrated into these same parts are suture loop tensioning means, and means for measuring and displaying the tension in the suture loop. FIG. 6A illustrates an exploded isometric view of another alternative tensioning device. FIG. 6B illustrates an isometric view of the device shown in FIG. 6A, wherein a cover (and other exterior parts) prevent viewing of the interior mechanisms of FIG. 6A.

FIG. 7 relate to a helical drive shaft and pinion embodiment, of suture tightening device;

As seen in FIG. 1, the method under this invention follows the following procedure;

Figure 1:
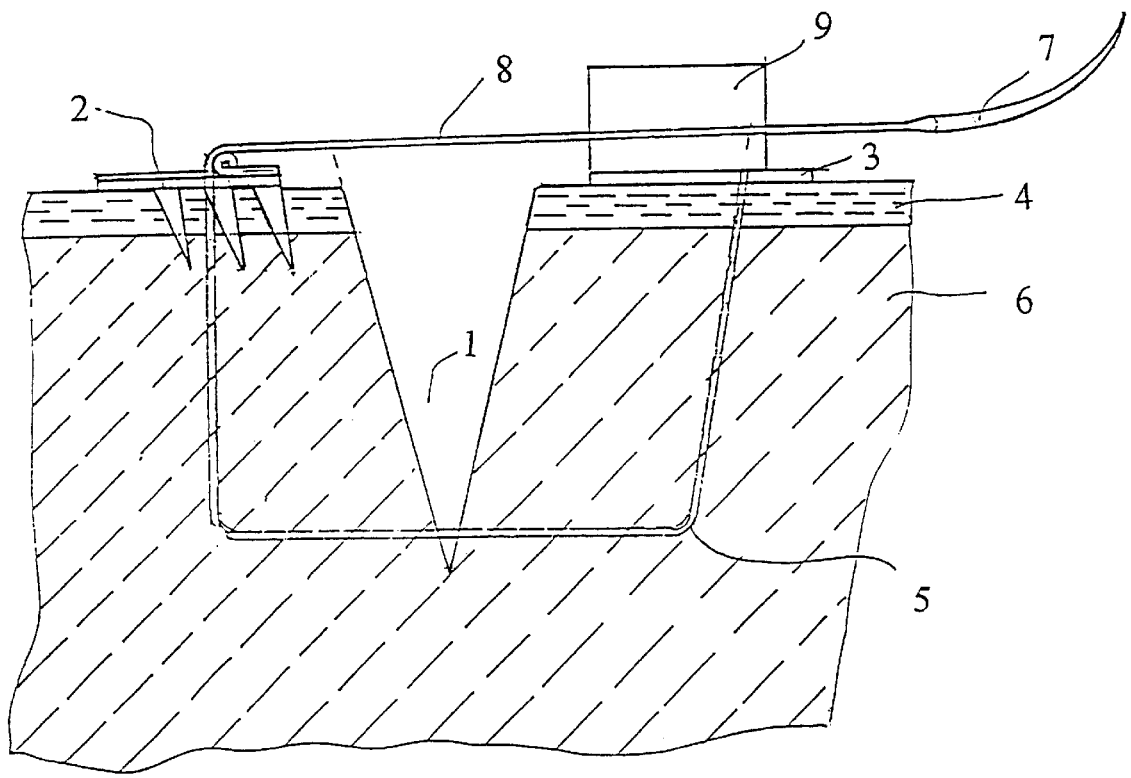
FIG. 1 illustrates a cutaway side view through a section of tissue in which the method under this invention is presented.

A device comprising a suture band (5) with attached needle (7), tissue reinforcing means (2) and (3), and suture loop tensioning means (9) is prepared for the surgeon. The wound (1) is cleaned and reinforced, such as by staple (2) or sticker (3) which are connected to the skin (4) on both sides of the wound. A flat suture band (5) is then sewn through the skin and underlying tissue (6) using the attached needle. Sewing is done through the reinforcing staples or stickers. The tail end of the band is fixed to the tensioning means, and the band is pulled so that the tensioning means comes to rest either on the surface of the skin or on the reinforcing staples or on the stickers. The needle bearing head end is then threaded or clamped into the tensioning means, the free remaining length of the forming loop (8) of band is pulled through the device, and tension is applied to the band. The needle can than be sheared off the band, along with any unneeded length of band.

Manually the tension is then gradually increased. Preferably, the tensioning means also has means for measuring, displaying, and limiting the tension to an allowed safe value. The tightened loop is then left in this state for a few minutes for the tension to subside by the skin self relaxation process which diminishes the width of the wound. The waiting time can be used for administering to other such devices in use along other portions of the wound or for attending to other chores. When the specified wait is over, or when the measured tension in the band has subsided enough, the band is re tightened and the process repeated, as many times as may be required.

Figure 2A:
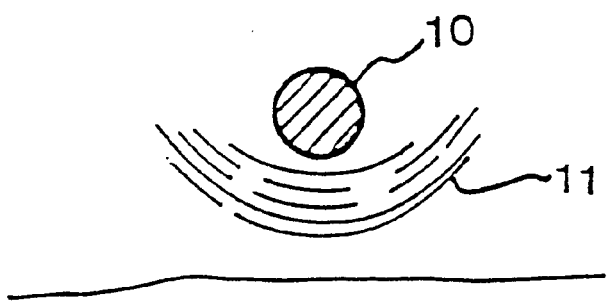
Figure 2B:
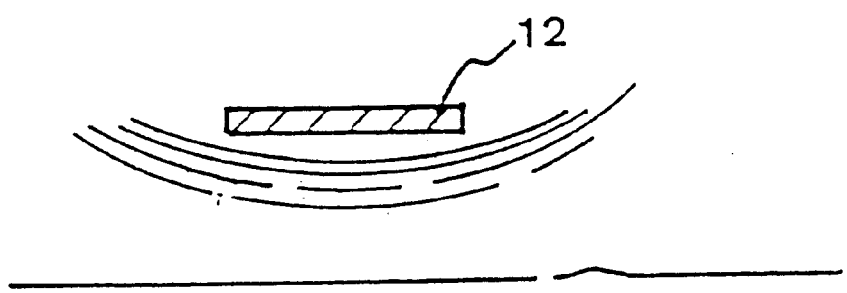
Figure 2C:
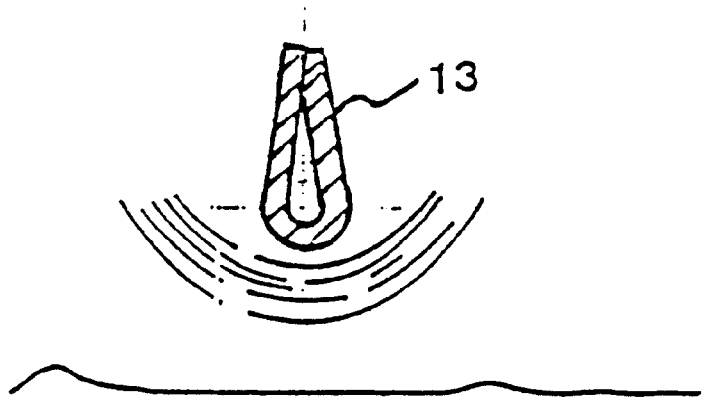

FIG. 2 relate to the relative stress concentration and tear mode for a circular pin or thread (FIG. 2A), a flat band (FIG. 2B), and a flexible band which is buckling under tension (FIG. 2C). In FIGS. 2, the stress concentrations in tissue of these suture types when tightened is shown. These stress concentrations indicate that laceration may result upon suture tightening.

FIG. 2 are intended to illustrate why the preferred embodiment of the device of the present invention is by suture band which is flexible along it's length and resistant to bending along it's width. If this band buckling resistance is not present in the suture, then band does not function much better than the plain thread suture.

FIG. 2A shows the stress concentration around a circular pin or thread (10). When tightened stress contours (11)

develop, composed of tension and compression, causing local stresses some 7 to 9 times grater than if the pull was evenly distributed over the skin/tissue (even higher for thinner threads). The tension tears the skin in front of the thread, and the thread moves forward so the tear continues to propagate towards the wound edge, leaving a laceration where the thread used to be.

FIG. 2B shows the stress concentration made by a band shaped suture (12) when the band is flat and perpendicular to the direction of the pull. As can be seen, the stress is more evenly spaced and distributed, thus lower and safer.

FIG. 2C shows what happens when a band suture buckles (13). Now only a smaller center portion of the band transmits most of the load, and the effect is similar to that of a circular thread, albeit of a relatively big diameter. The stress concentration is now more pronounced, and tends to buckle the band even further.

Figure 3:
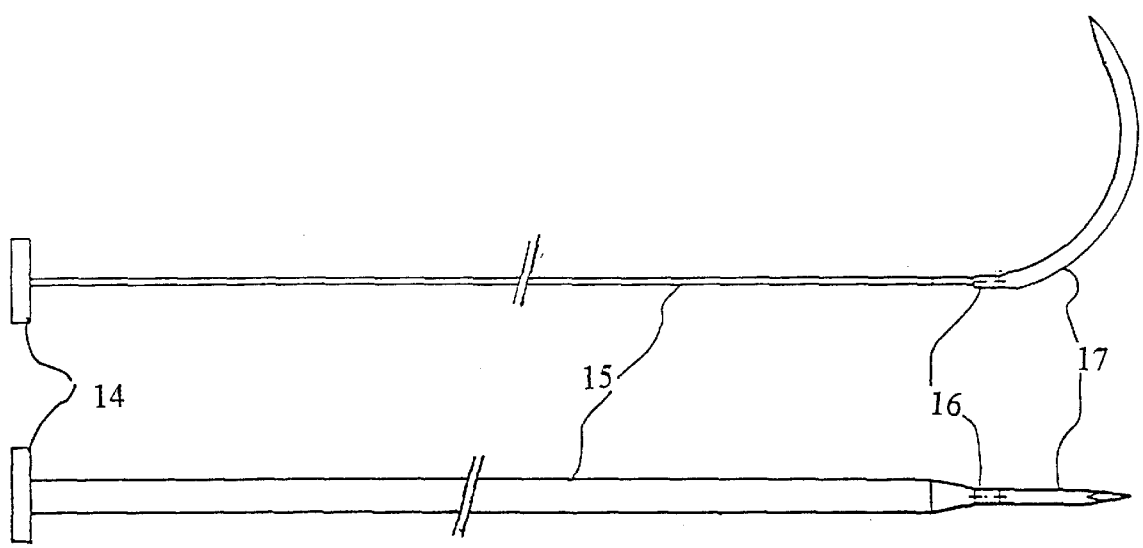

FIG. 3 illustrates two perspective views showing a flat mono-filament suture band. In FIG. 3, a preferred embodiment of suture band (15) is seen, where the band has an enlarged section (14) at the tail end, to dispense with the need to tie a knot in the band. At the head end, a less flat portion (16), which may be round, is set to receive a clamped-on surgical needle (17). The clamped-on surgical needle may be integrally attached to the suture. The surgical needle may be of any standard shape, such as the rounded type, ⅜ curve (shown), straight type, etc.

Figure 4A:
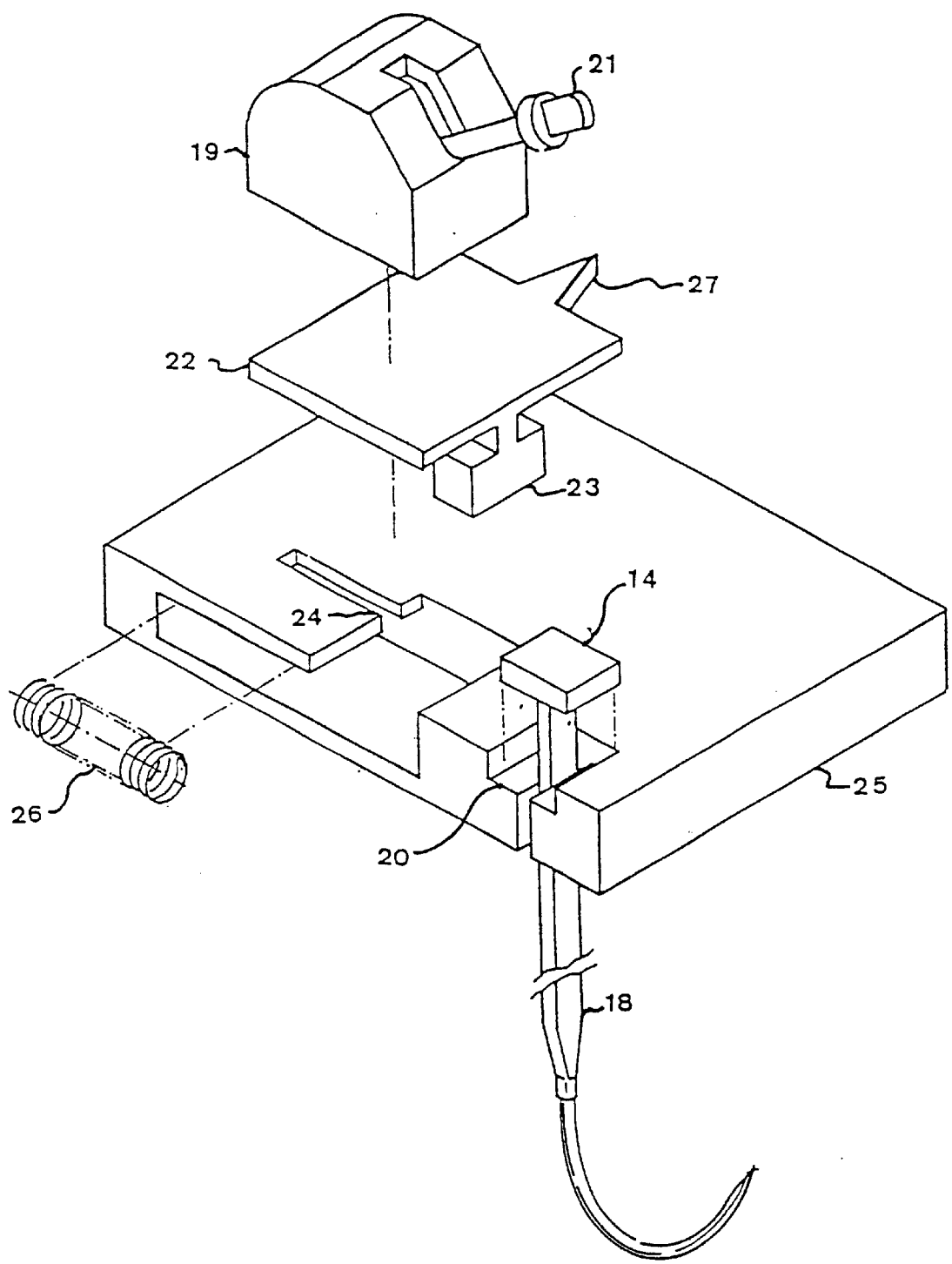
Figure 4B:
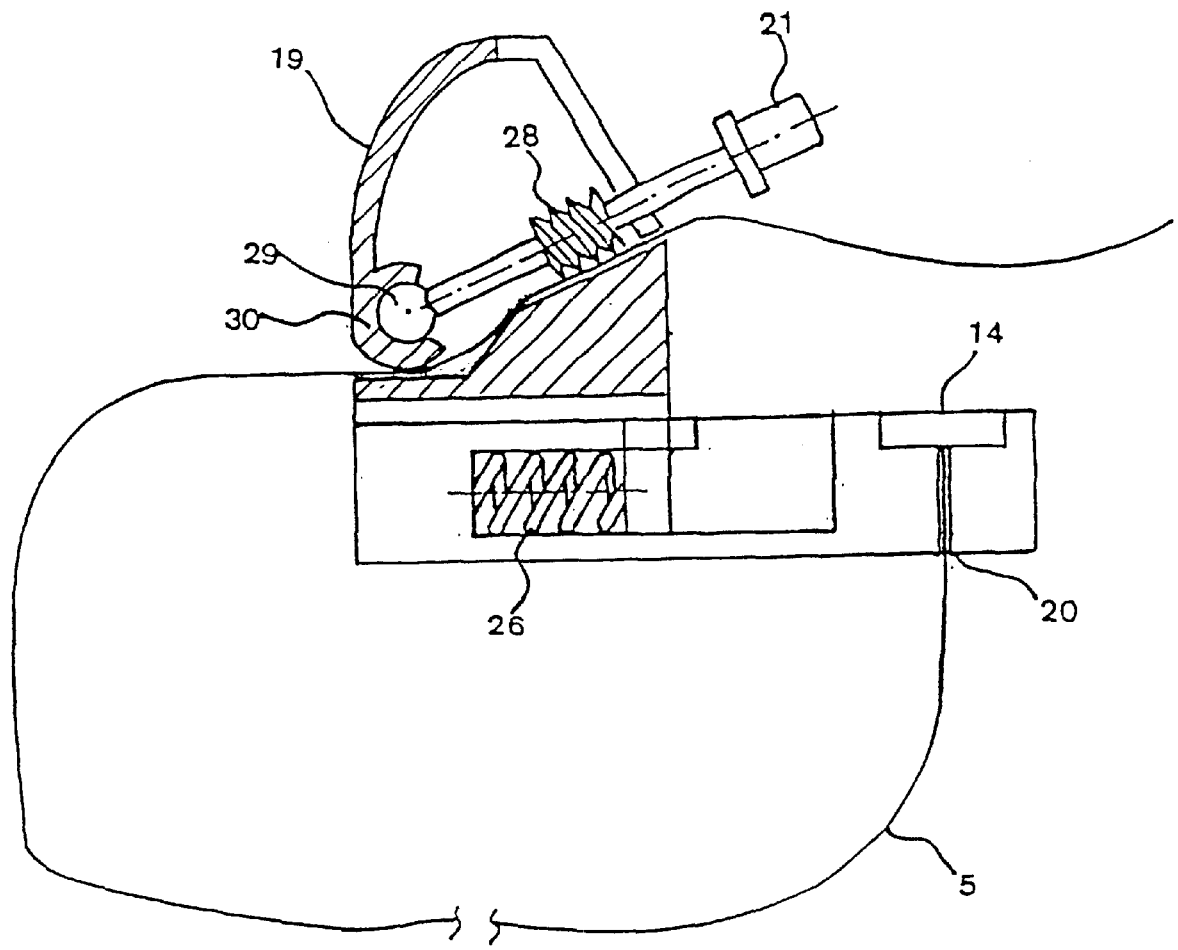
Figure 4C:
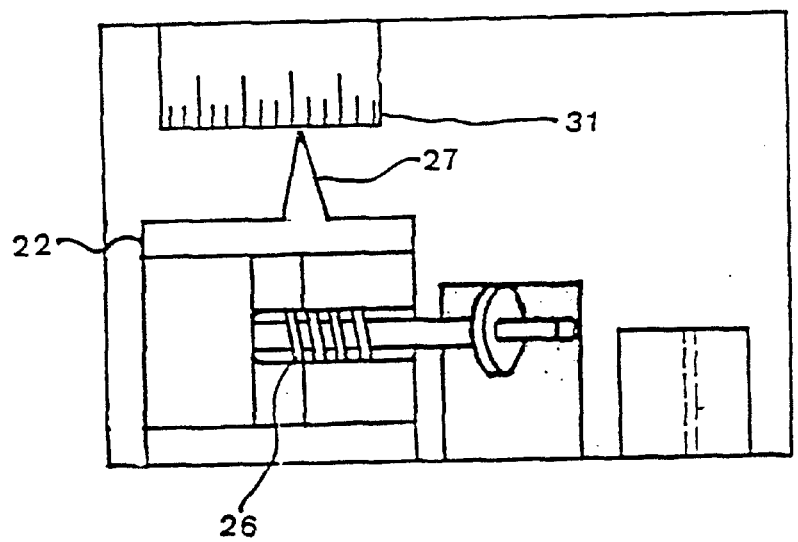

FIG. 4 relate to a lead screw embodiment suture tightening device. FIG. 4A is an exploded isometric view of a suture tightening device. FIG. 4B illustrates a cutaway side view through the suture tightening device (shown in FIG. 4A) for applying, measuring, and retaining of tension. In FIG. 4C, the means for measuring and displaying tension in the suture loop is shown from above.

FIG. 4A illustrates an exploded isometric view of a suture tightening device. A suture tightening wound closure device, comprising a smooth suture (18) and a suture loop tension means for closing the wound by grasping the first (tail) end of the suture and pulling back the second (head) end of the suture, characterized by the tension means having a manual control mechanism (19) for pulling or releasing the second end. The tension means is shown above a means for measuring and displaying the tension in the suture loop (which is integrally attached to the suture loop tension means).

The suture loop tension means is comprised of a suture ends holder assembly (having two openings for passing respective suture ends through), a clip (20) located at one of the openings for grasping the first end of the suture (14), a reversible lead screw located above the other opening for applying or releasing wound closing tension through the passing second end of the suture, and means for manually turning (21) said screw (being a knob in the present illustrated embodiment). The knob may be wide and flat, or of any other convenient shape for ease of turning by the surgeon, who must use it to apply the necessary suture loop tension.

The manual control mechanism (19) is firmly attached to the tension indicator plate (22). From the lower face of this plate protrudes a slide profile (23) which fits into a corresponding groove (24) on the base plate (25). A spring (26) in the base provides a predetermined resistance to the motion of the indicator plate with respect to the base plate. This resistance in juxtaposition to the tension in a suture loop determines the exact location of the indicator plate arrow (27), and thus the amount of tension in a suture loop may be observed by the surgeon.

The base plate and indicator plate together form the tension measuring and displaying means, while the manual control mechanism and the base plate together form the suture loop tensioning means.

FIG. 4B illustrates a cutaway side view through the suture tightening device (shown in FIG. 4A) for applying, measuring, and retaining of tension, comprised of a suture loop tensioning means having a manual control mechanism (19), and a suture band (5). The tail end (14) of the suture band has been fixed in the holder, and the head end (having been sewn across the open wound) passes through the tensioning means of the holder. Thus the assembly has two openings for passing respective suture ends through. The assembly has a clip opening (20) for grasping the tail end of the suture band, a reversible lead screw (28) for applying or releasing wound closing tension through the passing head end of the suture, and a knob (21) for manually turning the screw. There is a spring (26) located in the base of the assembly such that when tension is applied to the suture band loop, the tensioning suture head holder compacts the spring for measuring the tension.

The holder facing end of the screw is ball profiled (29), and a ball joint socket (30) with an elongated opening located in the holder holds the ball end of the screw, allowing the (vertical) angle of the screw in the holder to be manually switched to either an open position (up) for the complete release of applied tension to the suture loop, or to a closed position (down) for the complete prevention of any release of excess tension in the suture loop.

In FIG. 4C, the means for measuring and displaying tension in the suture loop is shown from above. The manual control mechanism is firmly attached to the tension indicator plate (22). A spring (26) in the base provides a predetermined resistance to the motion of the indicator plate with respect to the base plate.

This resistance in juxtaposition to the tension in a suture loop determines the exact location of the indicator plate arrow (27), and thus the amount of tension in a suture loop may be observed by the surgeon as the arrow points to a scale of suture loop tension (31).

Thus, FIG. 4 should together be viewed as a single embodiment of the present invention. The base plate should have filleted corners on the bottom side so as not to scratch the skin onto which it is placed. The groove (24) in which is nested a spring (26), the slide profile (23), and the notched scale (31) fixed to the base, are together composing a dynamometer for measuring and displaying the suture loop tension.

With the knob pulled up, the screw is tilted out of the way, allowing the band suture head end to be threaded through the manual control mechanism, with or without the suture head end needle. When the knob is then pressed down, the screw engages the suture band, and turning the knob will advance the band forward or reverse. Thus tension can be added or reduced in precise increments. With the suture band under tension, the manual control mechanism will be pulled towards the wound on the sliding profile (23), until the reaction force from the spring counteracts the pull of the suture band. The slider points to a position indicative to the tension in the band, allowing it to be read on the scale of suture loop tension (31).

Figure 5A:
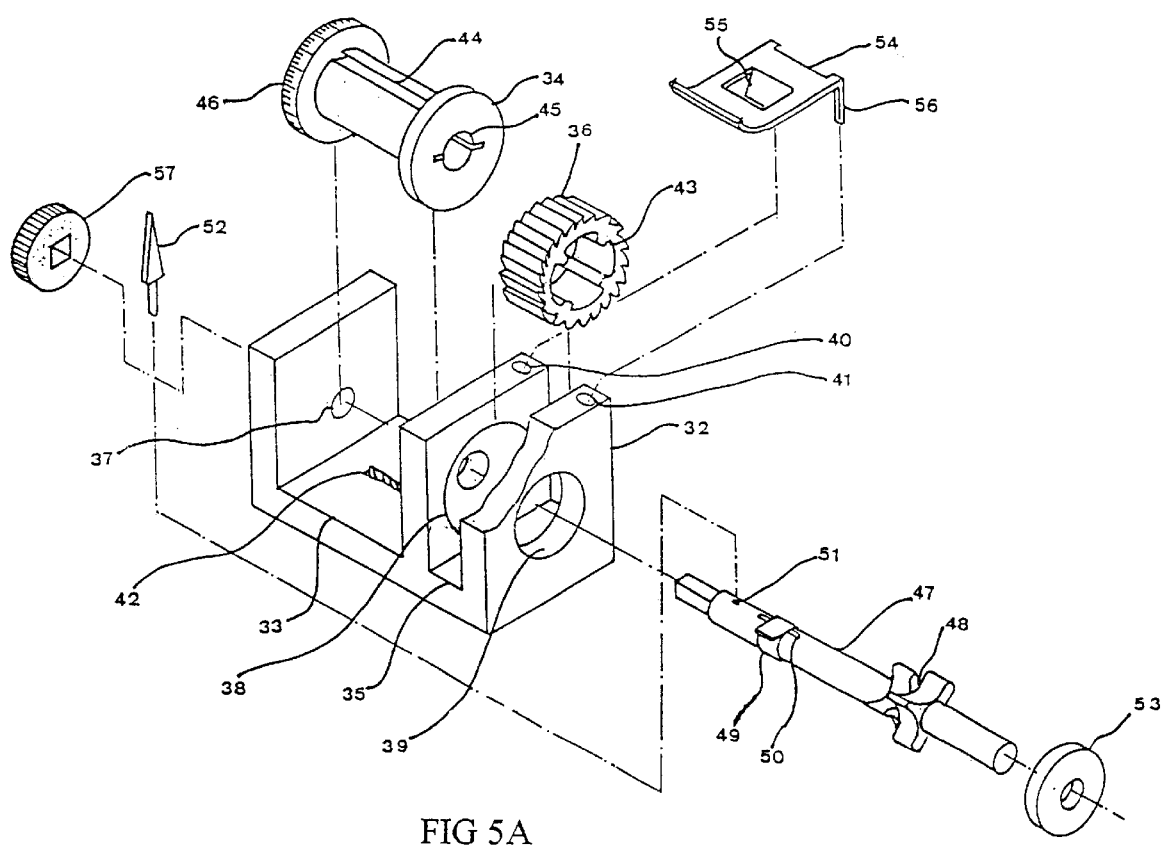
Figure 5B:
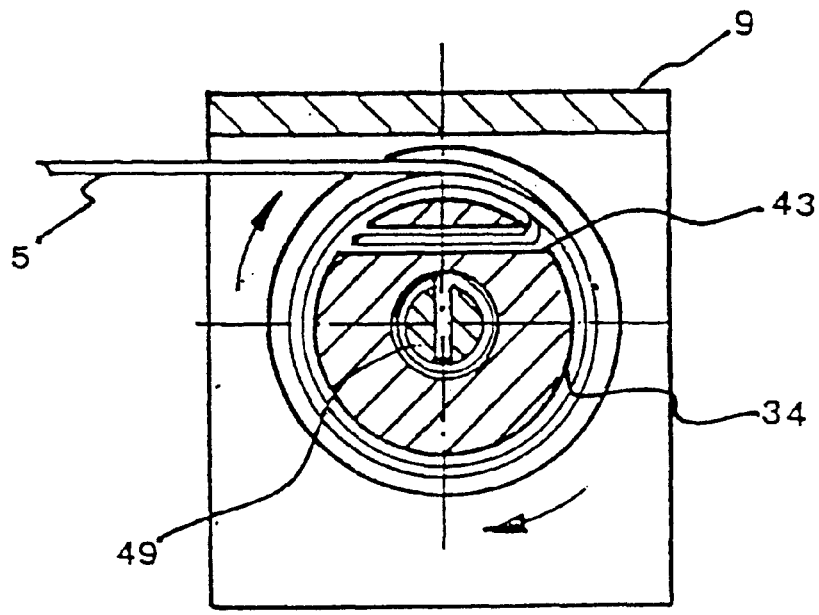
Figure 5C:
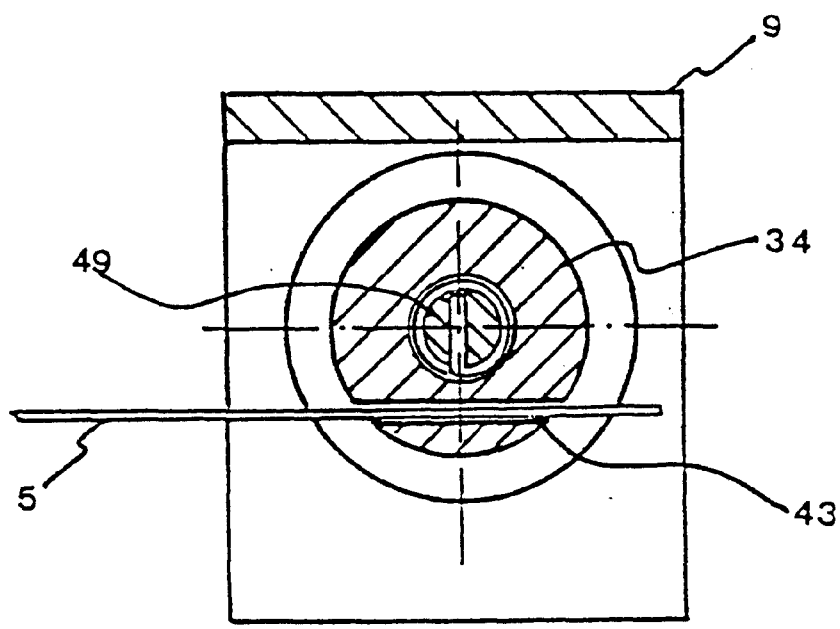

FIG. 5 relate to an alternative embodiment of a "ratchet drum" manual control mechanism for applying or releasing tension through the attached or passing head end of a suture, wherein a tension measuring and displaying means has been incorporated. FIG. 5A illustrates a perspective exploded view of the ratchet drum device for applying, measuring, and retaining of tension, with the incorporated tension measuring means. FIG. 5B illustrates a suture end attached to a ratchet drum. FIG. 5C illustrates a ratchet drum with a passing head end of a suture.

FIG. 5A illustrates a perspective exploded view of the ratchet drum device for applying, measuring, and retaining of tension (with the incorporated tension measuring means) comprised of;

A ratchet assembly holder (32) with a wide opening (33) to hold a drum (34) and a narrow opening (35) to hold a ratchet (36) while allowing both to rotate. The wide opening is nominally wider that the length of drum. A hole (37) extends the entire length of ratchet assembly holder, perpendicular to the two openings and bisecting them. A predetermined distance before bisecting the narrow opening, the hole enlarges in diameter forming a cup (38). On the outer side of the narrow opening the enlarged diameter hole has tapped thread (39). Two holes (40) (41) are set into the top of the ratchet assembly holder, and an elongated hole (42) is set through the bottom of the wide opening.

Ratchet (36) wheel has a central hole (43) made in the form of a circular hole with evenly spaced teeth protruding inwards, the ratchet wheel is placed into the narrow opening (35).

Drum (34) has a groove (44) in the form of an arc chord and a central hole (45) in the form of a circular hole with opposing grooves. On one side of the drum, a dial (46) is printed. The drum is placed in the wide opening (33).

A shaft (47) has a crown (48) composed of two sets of evenly spaced outwardly protruding teeth, the outer radius of said teeth matching the radius of holes (39,38,43) in the other parts, the number of teeth in each set and the angle of which matching the teeth of hole (43), the face width of the teeth matching the dimension of the interior bore of the ratchet, and one set being rotated at an angle of half a tooth spacing in relation to the other set. The shaft is inserted through hole (37) all the way to hole (39), in the process capturing ratchet (36) and drum (34). A leaf spring (49) is passed through groove (50) in the shaft and into grooves (45) in the drum bore. A pointer (52) is placed in hole (51) in the shaft so as to point over dial (46) of the rack. A washer (53) with external thread and is placed into hole (39) to prevent shaft (47) from escaping (while letting it rotate and slide back and forth).

A leaf spring pawl (54) has a curled edge (55) at one end and two legs (56) (second leg not seen) at the other end, which are inserted into holes (40) (41). The leaf spring pawl now secures ratchet (36) as long as curl (55) is not manually pulled up.

In normal operation, a suture band passes through an opening (not shown) in the base plate and a clip (not shown) is located at the opening for grasping the band tail, the suture is sewn across the wound, and the suture band head end is inserted in hole (42) and pulled onto or through the drum (after the attached needle is clipped off). The shaft (47) is then rotated, using a wrench or snap-on knob (57) over the flat section end of the shaft. The torque is transmitted through leaf spring (49) to the drum, pulling the band, which curls around the rack (as seen in FIGS. 5B or 5C) and tensioning begins with the band close to skin level. Meanwhile, the banding of spring (49) under the torque causes an angular deflection between the rack (with its dial (46)) and shaft (with its mounted pointer (52)). Teeth (48) on the shaft engage teeth (43) on the ratchet bore, and drags the ratchet along, with the spring pawl (55) skipping over the outer teeth of the rotating ratchet (36).

If the need arises to diminish the tension, two ways are available;

A complete release, by manually pulling up of the spring pawl (54), causing it to disengage letting the ratchet counter—rotate freely.

A controlled release, by pushing shaft (47) back and forth, using the button—like protrusions left poking through washer (53) and hole (37). This causes one set of teeth (48) to move to the side into the recesses of the ratchet bore until it disengages teeth (43) and the shaft rotates a half-tooth-angle until teeth (43) meet and engage the other set of teeth (48). During the process the ratchet is secure and not rotating. The process may be repeated many times as long as tension is kept in the band.

FIG. 5B illustrates a suture end attached to a ratchet drum. A suture loop tensioning means (9) into which has been inserted the head end of a suture band (5) is shown. Inside the tensioning means is a drum (34) having a groove (43) in the form of an arc chord. The suture head end is inserted into the groove, and the drum is wound such that the suture band wraps around the drum, thus holding the inserted head end of the suture firmly. This firm holding of the suture head end allows the drum to be further used for suture loop tensioning.

Note that in the context of this figure, the suture loop head end has had any attached surgical needle sheered off. Other embodiments of the drum allow the needle to be placed into the groove as initiation of the firm holding of the suture by the drum procedure. At the center of the drum is the leaf spring (49), the function of which is better understood from FIG. 5A.

FIG. 5C illustrates a ratchet drum with a passing head end of a suture. A suture loop tensioning means (9) into which has been inserted the head end of a suture band (5) is shown. Inside the tensioning means is a drum (34) having a groove (43) in the form of an arc chord. The suture head end is inserted through the drum by way of the groove until a nominal tightness in the suture loop is felt, and the drum is then wound such that the suture band wraps around the drum, thus holding the inserted head end of the suture firmly. This firm holding of the suture head end allows the drum to be further used for suture loop tensioning. Note that in the context of this figure, the suture loop head end need not have any attached surgical needle sheered off. At the center of the drum is the leaf spring (49), the function of which is better understood from FIG. 5A. Use of the drum for hand pulling the excess suture length through the tensioning means speeds the process of starting the suture loop tightening.

Thus, FIGS. 5 should together be viewed as parts of a single embodiment of the suture loop tensioning means, wherein the means for grasping the tail end of the suture is not shown. The parts shown of the suture loop tension means is comprised of a suture ends holder assembly, said assembly having an opening for holding the second (head) end of the suture, a ratcheted drum located above the this opening for applying wound closing tension through the attached or passing second end of the suture, and means for manually turning the drum. Also integrated into these same parts of the suture loop tensioning means is in addition a means for measuring and displaying the tension in the suture loop.

FIG. 6 relate to another alternative tensioning device. This is part of a non-ratcheted drum embodiment of the present invention. Also integrated into these same parts are suture loop tensioning means, and means for measuring and displaying the tension in the suture loop.

Figure 6A:
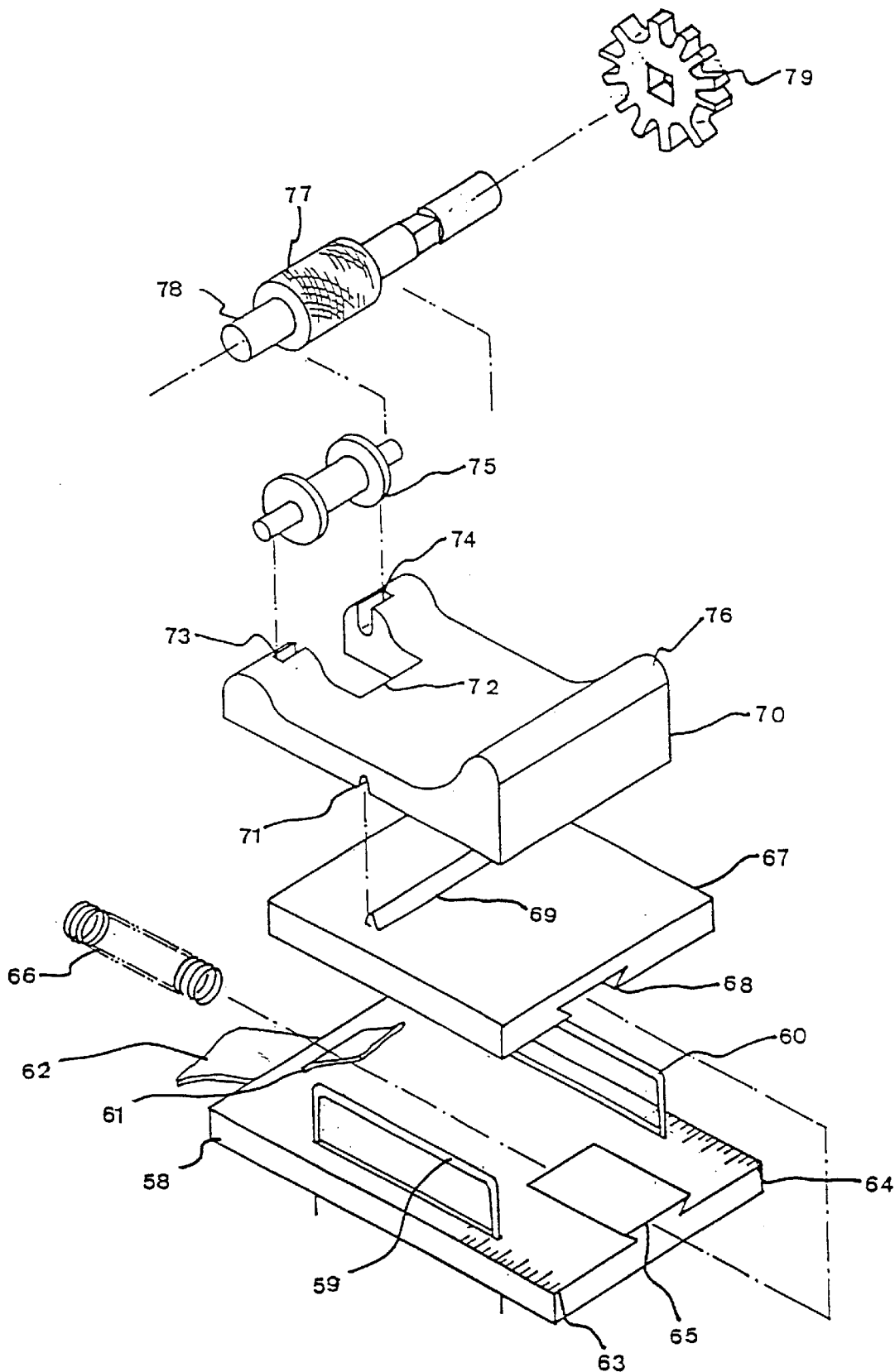

FIG. 6A illustrates an exploded isometric view of another alternative tensioning device. This device for applying, measuring, and retention of tension is comprised of;

A suture reinforcing means base (58) for placement against the skin on one side of an open wound, having two skin piercing staples (59) (60) incorporated therein (which pass through the reinforcing means base and into the skin and tissues thereunder), an opening (61) through which the tail end of a suture band (62) is attached, parallel suture loop tension measurement scales (63) (64), a protruding trapezoidal slider track (65) on which the next layer (67) (tension means base) of the device rests and slides, and a tension spring (66) for pulling (or in another embodiment pressing) against the sliding motion of the next layer part (67) (tension means base) so that a predetermined resistance to sliding can be observed as the measured tension in the suture band loop.

A tension means base (67) having a conformable sliding groove (68) for sliding on the trapezoidal slider track (65), a holding clip (not seen) on the under side for pulling (or pressing) against the side of the tension spring (66) furthest from the trapezoidal slider track, and a pivot support (69) onto which the next layer part (70) (swivel rocker) is placed.

A rocker (70) having a transverse groove (71) on the under side for pivoting and rocking on the pivot support (69), a fork opening (72) with opposing groves (73) (74) wherein the axle ends of a roller (75) rest and turn, and a juxtaposed transverse protruding hump (76) which in conjunction with the roller gives the swivel rocker the shape of a saddle.

A drum (77) (with a rough exterior for providing friction when turned against the surface of a suture band) is attached to a shaft (78), and a pinion gear (79) on the end of the shaft will allow controlled turning of the drum.

Figure 6B:
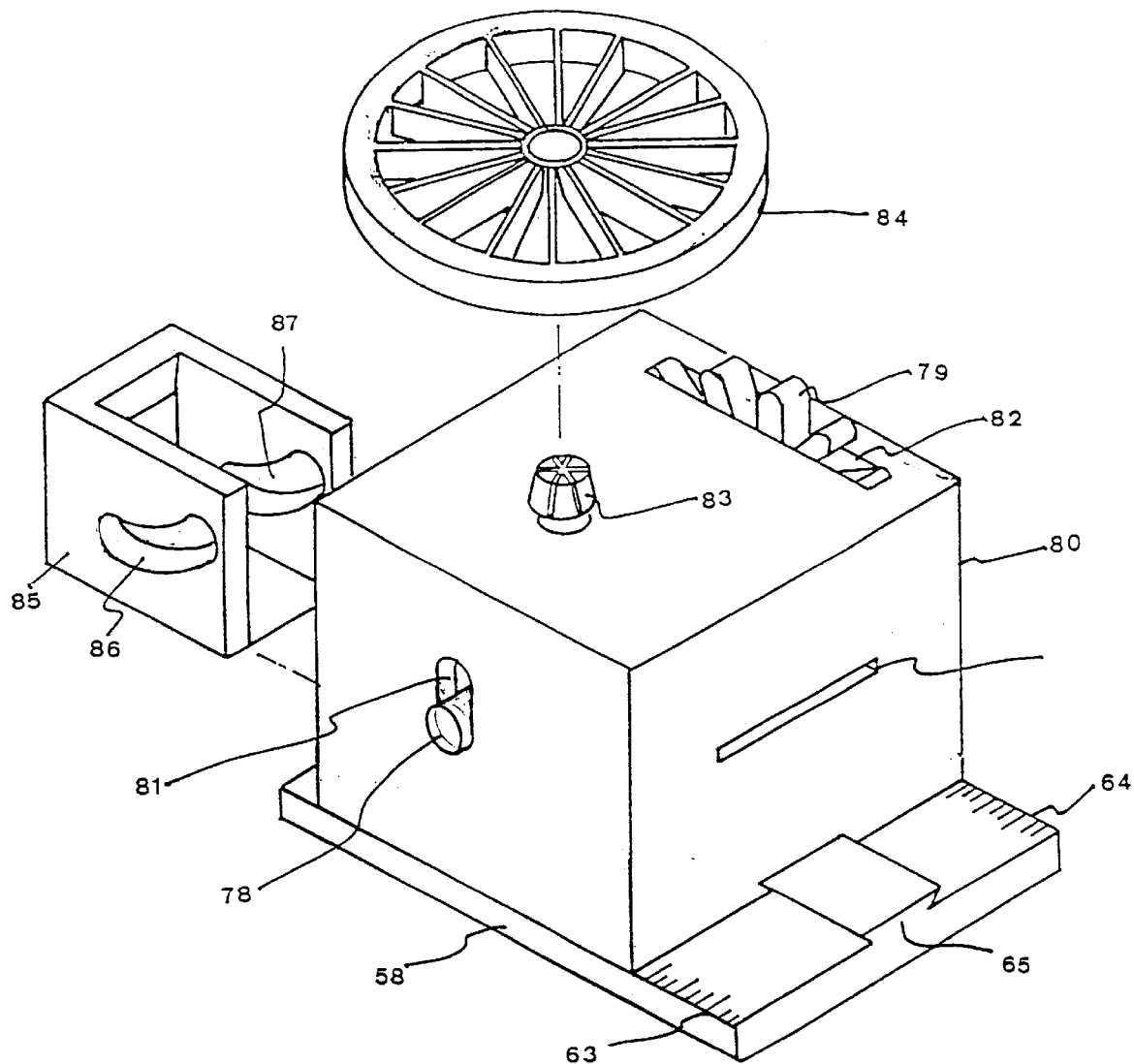

FIG. 6B illustrates an isometric view of the device shown in FIG. 6A; wherein a cover and other exterior parts prevent viewing of the interior mechanisms shown in FIG. 6A. Summarizing FIG. 6A, a suture band is sewn across an open wound through the skin and underlying tissue, the tail end (62) is attached to the reinforcing means base (58), the head end (not shown) (with the surgical needle removed) is passed through a opening in the cover (shown in FIG. 6B), over the hump (76), under the drum (77), over the roller (75), and out of the box through an opening on the back side (not shown).

Having passed through the device, the head end of the suture band may be pulled until a nominal tension is observed, thereafter the pinion gear (79) (or exterior parts attached thereto) are used to apply or release tension from the suture band loop. Note, the swivel rocker pivoting motion prevents both rapid pulling on the suture head end and rapid release of tension through the suture head end, because the rough surface of the drum will either semi-lock the band against the roller or against the hump (according to the angle of the pivot rocker).

FIG. 6B illustrates an isometric view of the device shown in FIG. 6A, wherein a cover and other exterior parts prevent viewing of the interior mechanisms of FIG. 6A. A suture reinforcing means base (58) with parallel suture loop measurement scales (63) (64), and a protruding trapezoidal slider track (65) are shown.

Resting on this suture reinforcing means base is a hollow box body (80) having two elongated side openings (81) (second opening not seen) through which the shaft (78) ends protrude. At the top of the hollow box body is another elongated opening (82) through which part of the pinion gear (79) teeth projects. Also at the top of the hollow box body is a vertical axial support (83) on which rests a crown gear (84). Turning of the crown gear results in turning of the pinion gear. The crown gear, being parallel to the skin surface, may be of a larger diameter than the pinion gear without effecting the overall size of the device (which is essentially scaled according to the suture band width). This larger diameter crown gear is easier to manually turn than the smaller pinion gear.

A "U" shaped locking tab (85) having two parallel arched opening (86) (87) is slid over the sides of the hollow box body, and the protruding shaft ends also protrude through the arched openings. This locking tab (when pulled) forces the interior drum up resulting in the freeing of any constraint by the device on the head end of the suture band. Pushing the locking tab forces the interior drum to press into either side of the saddle shaped pivot rocker, resulting in the capacity to control the tightening or releasing of tension in the suture loop. An optional pawl (not illustrated) would prevent the crown and pinion gears from counter-rotating under any tension on the suture, or provide an audible "click".

FIG. 7 relate to a helical drive shaft and pinion embodiment, of a suture tightening device. In this embodiment, the suture loop tension means is comprised of a rigid casing(90), having;

(a) three suture passage openings (105)(109)(120);
(b) a clip (103)(104) located in the casing near one (120) of said openings, for invariably grasping one end of the suture;
(c) a helical drive shaft (91) and pinion (92) mechanism inside the casing, for applying a controlled wound closing tension to the suture loop;
(d) means (94) for manually turning said helical drive shaft clockwise or counterclockwise for driving the suture and controlling its tension;
(e) locking mechanism comprising a locking handle (96) and a locking lever (111) inside the casing for locking and unlocking the suture band second end;

In the locking position of the locking mechanism, the suture loop tension is under the control of the helical drive shaft rotation, and in the unlocking position of the locking mechanism, the suture tension is released, allowing hand pulling it through two (105)(109) of said three suture passage openings.

Figure 7A:
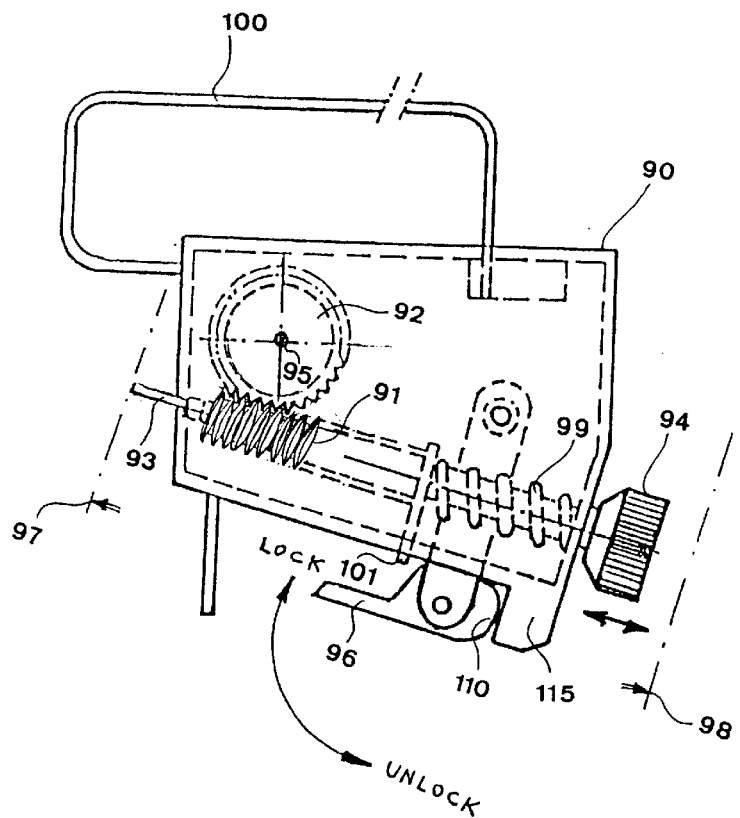
FIG. 7A illustrates a side view of the device, facing the helical drive shaft and pinion.

FIG. 7A illustrates a side view of the device, facing the helical drive shaft. The device comprises a casing (90), there affixed a helical drive shaft and pinion mechanism. A pivot (93) is penetrating through two opposing walls of the casing (90), where a pair of bearings are fixed, enabling the pivot to rotate free. A helical drive shaft (91) is fixed along a portion of said pivot, and linked with a pinion (92). The pinion (92) is rotateable around an axle (95) which passes transversely to the pivot (93). Next to the pinion (92), on the same axle (95), is fixed a suture drive wheel (not shown in this figure). The pivot (93) ends in one of its two edges with a controlling knob (94), such that rotating the controlling knob (94), rotates the pivot (93) and drives the pinion (92) by means of the helical drive shaft (93). Correspondingly, the suture drive wheel (which rotates on the same axle (95) of the pinion (92)) drives the suture (100) inside or outside the casing, relatively to rotating the controlling knob (94) clockwise or counterclockwise.

Controlling the suture and driving it by rotating the controlling knob, functions only when the suture locking mechanism is set "lock" (i.e. when the locking handle (96) is in the "lock" position, as is in this figure). Otherwise (when the locking handle is set "unlock"), the suture can freely move through the device (for a detailed description concerning the operation of the locking mechanism see FIGS. 7B–7D).

In addition to the rotational motion which the pivot (93) is provided with, this pivot can also slide back and forth, along its longitudinal direction. This longitudinal motion is restricted between two predetermined limits (97)(98). The restriction is achieved by means of protrusions or widenings along the pivot, which are prevented from passing through the bearings through which the pivot passes, rotates, and slides back and forth. A back and forth movement of the pivot (93) (without rotating it), slightly rotates the pinion by the helical drive shaft (91). Thus, the helical drive shaft (91) may act in rotating the pinion (92) in two different ways: a) by pivoting (endlessly), and b) by moving back and forth (within limits (97)(98)). There is no mutuality in the relations between the helical drive shaft (91) and the pinion (92), since the pinion may act in driving the helical drive shaft only in one way. A slight rotation of the pinion back and forth, shifts the helical drive shaft (91) (together with pivot (93)) back and forth, within the limits (97)(98). However, causing rotational movement of the pivot (93) by the rotation of the pinion (92) is impossible, due to the effectiveness of inclined-plane mechanical advantage of the helical drive shaft, upon the pinion.

The pivot (93) is provided with spring (99), pushing it toward the limit (97). In contrary, the tension of the suture (100) (when in position, reinforcing a wound), acts to rotate the suture drive wheel (not seen in this figure) and the pinion (92) (which both are fixed on the same axle (95)) counterclockwise, thus pushing the pivot (93) toward the opposite limit (98).

The spring (99) is designed with such springiness, such that when the tension of the suture (100) is average (according to medicine considerations), the pivot (93) reaches the mid position between the two limits (97)(98). A pointer (101) is connected to the pivot, and aligned against a suture loop tension indicator scale (not shown in this figure), forming a tension measuring and displaying means. In this embodiment the scale is marked on an exterior wall of the device, along the potential movement path of the pointer (101). The actual position of the pointer relatively the scale indicates the actual tension in the suture band.

Figure 7B:
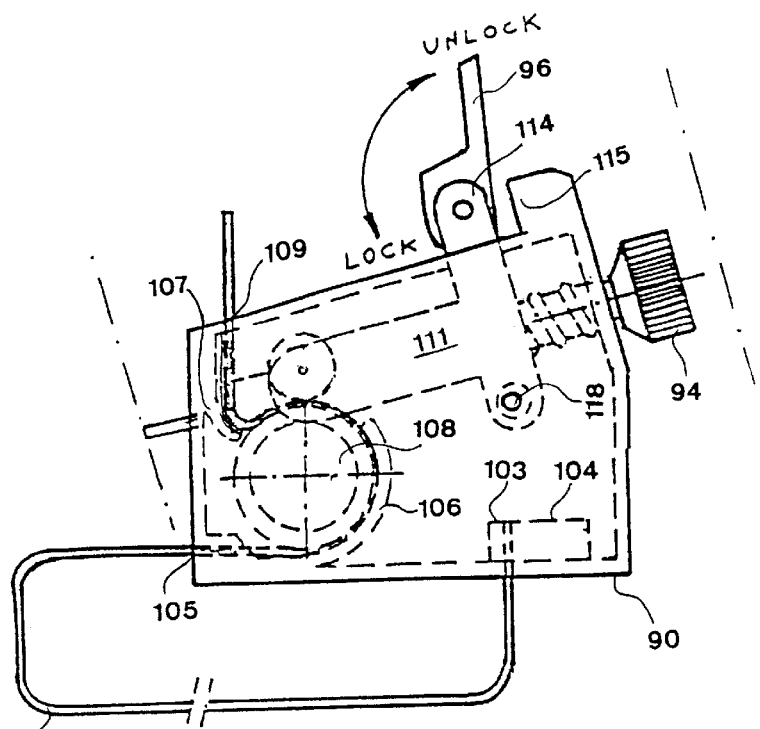
FIG. 7B illustrates a side view of the device, facing the suture locking mechanism.

FIG. 7B illustrates a side view facing the suture locking mechanism of the device. The tail end of the suture band (100) is fixed inside the device, by force of screws (not seen in this figure) pressing two pressing-plates (103)(104) together, and the tail of the suture among. The suture band is then swan and looped through the skin and underlying tissue of a wound. The head end of the suture is then inserted to the device through a first opening (105), and guided by guiding protrusions (106)(107) to encircle the suture drive wheel (108) and to exit the device through a second opening (109). In this figure, the locking handle (96) is in the "unlock" position, which is the appropriate state for inserting the head end of the suture band into the device as herebefore described, and then to pull this free head end, tightening the loop (and the device) around the wound. To complete the procedure, the locking handle (96) has to be set to the "lock" position. The lock position is an ultimate operative state for driving the suture band (100) under the control of the controlling knob (94). Furthermore, only in the "lock" position the tension measurement mechanism is operative.

The "lock" state of the locking mechanism controlled by the locking handle (96), is characterized by preventing free movement of the suture band through the device on one hand, but on the other hand, allowing bi-directionally driving the suture band, by rotating the knob (94) clockwise or counterclockwise, according to need.

The locking mechanism of the device (according to the present embodiment), is comprised of a pivoting lever (111) having a locking-handle-arm (114) which on its end is pivoting the locking handle (96), and having pressure-wheel-arm (119) which on its end located a pressure wheel (112) on an axle (116). A cog wheel (113) (not seen in this figure) is integrated next to said pressure wheel (112) on the same axle (116). The lever (111) is arranged to pivot around fulcrum (118), which actually is an axle, fixed between two opposing walls of the casing (90). However, the range for the lever to pivot is small, and limited between two contrary positions: one position is when the end of the locking-handle-arm (114) of the lever is blocked by extension (115) (this extension is made from the body of the casing), and the second position is when the pressure wheel (112) (on the end of the pressure-wheel-arm (119) of the lever) is pressed to the suture drive wheel (108) with the suture band (100) among.

When the locking handle (96) is set "unlock" the lever (111) has free movement within said range, no pressure is produced by the pressure wheel (112), and thus, the suture band (100) is released. It is different, when the locking handle (96) is set "lock". The locking handle has an arched back portion (110) (seen in FIG. 4a). In the "lock" position, the edge of the arched back portion (110) of the locking handle engages the extension (115) and forces the lever pivoting counterclockwise until the pressure wheel is well pressed to the suture drive wheel (108) and the suture band among. When the suture band is well pressed between both said wheels, it is locked and cannot move, unless the knob (94) is being rotated for driving the helical drive shaft (91), the pinion (92), and the suture drive wheel (108). The suture drive wheel (108) has an integral cog wheel (102) which (in the "lock" state) is geared with the integral cog wheel (113) of the pressure wheel (112), such that the motion of all the wheels is controlled solely by rotating the knob (94).

Figure 7C:
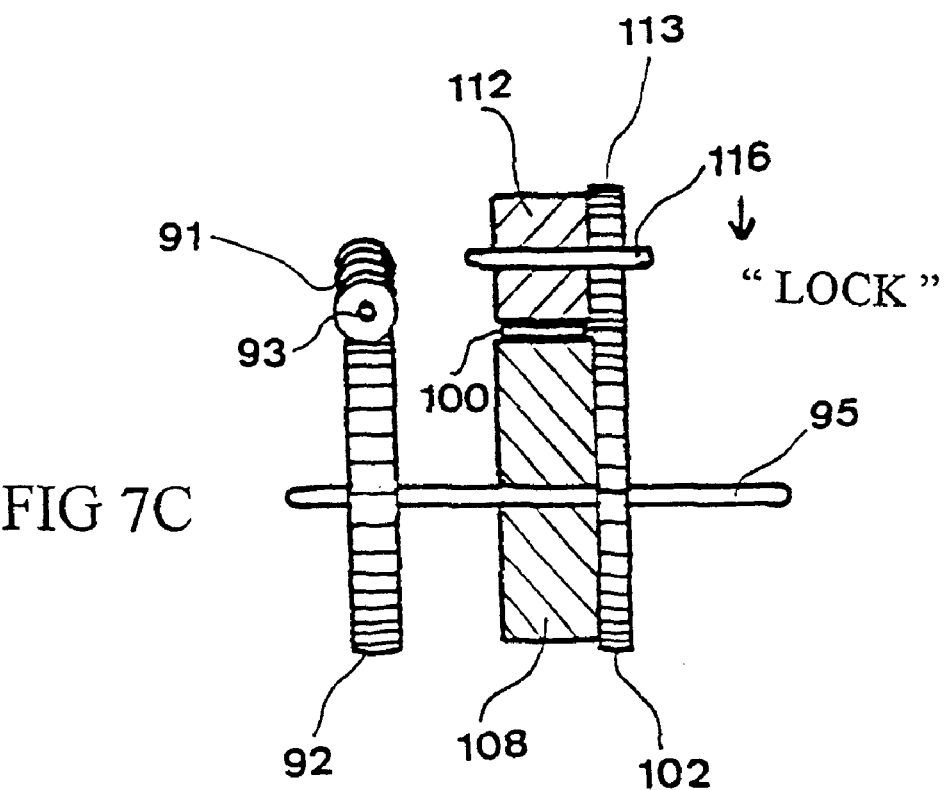
FIG. 7C illustrates a front view combined with a cross section view, of the locking mechanism of the device in a "lock" position, and a suture is locked within.

FIG. 7C illustrates a front view combined with a cross section view, of a part of the locking mechanism of the device. This figure illustrates the "lock" position (the suture (100), the suture drive wheel (108), and the suture pressure wheel (112), are illustrated in a transverse cross section view). The pressure wheel (112) and its integral cog wheel (113) are arranged on a common axle (116) (see FIG. 7B, for the location of the axle (116) on the end of the pressure-wheel-arm (119) of the lever (111)). The axle (116) is anchored to the lever (111) between two lateral arms having appropriate (bearings) holes for the axle, allowing it to rotate free. In the "lock" position, the pressure wheel (112) is enforced to the illustrated position, by the mechanism of the locking handle (96) and the pivoting lever (111). In this position, the suture (100) is stressed between the pressure wheel (112) and the drive wheel (108), such that its movement backwards or forwards, is conditional to the rotation of the drive wheel.

The drive wheel (108) rotation is achieved by the rotation of the helical drive shaft (91) clockwise or counter clockwise around the pivot (93), thus driving the pinion (92), and the common axle (95).

The integral cog wheel (102) of the drive wheel (108) is geared with the integral cog wheel (113) of the pressure wheel, such that actually, in the "lock" position, the movements of the suture (100) are controlled mutually by both the drive wheel (108) and the pressure wheel (112).

According to other variation of the present embodiment, the cog wheels (102)(113) are absent, and controlling the movements of the suture band (100) is achieved by the efficiency of the friction between the suture (100) and its two stressing wheels (108)(112).

Figure 7D:
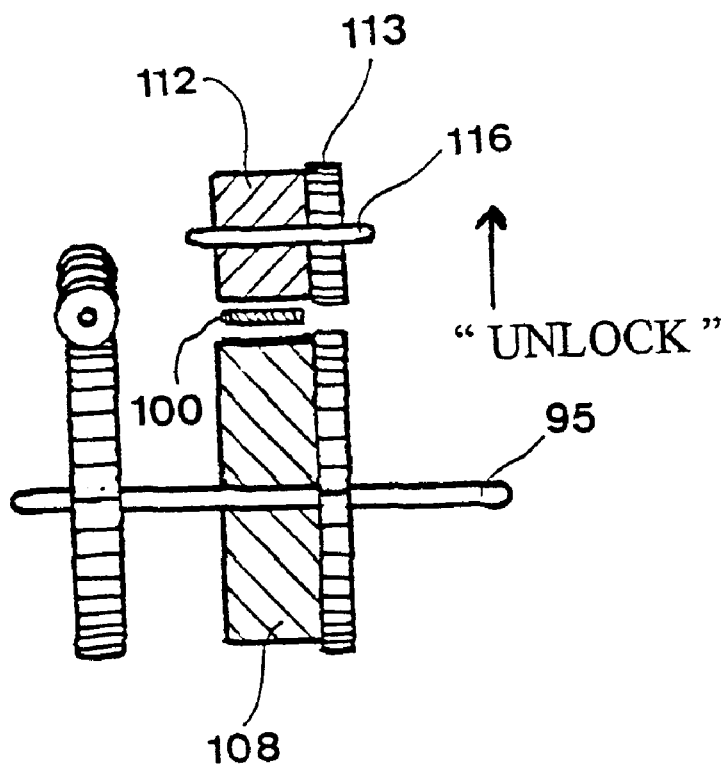
FIG. 7D illustrates a front view combined with a cross section view, of the locking mechanism of the device in an "unlock" position, wherein the suture is released between the suture drive wheel and the suture pressure wheel.

FIG. 7D illustrates a front view combined with a cross section view, of the locking mechanism of the device in an "unlock" position, wherein the suture (100) is released between the suture drive wheel (108) and the suture pressure wheel (112) (the suture (100), the suture drive wheel (108), and the suture pressure wheel (112), are illustrated in a cross section).

Releasing the suture (100) is achieved by turning the locking handle (96) to the "unlock" position, and thus releasing the lever (111) to pivot on its fulcrum axle (118) for raising the pressure-wheel-arm (119) with the pressure wheel (112) on its end, from above the suture (100) and the drive wheel (108).

What is claimed is:

1. A suture tightening wound closure device for use on mammals including humans, comprising a smooth suture (5) to be sewn across an open wound (1) through the skin (4) and underlying tissue (6), and a suture loop tension means (9) for closing the wound by grasping the first end of the suture and pulling back the second end of the suture, characterized by;

said suture loop tension means having a manual control mechanism, operated by a rotating component, for pulling or releasing said second end wherein said mechanism allows for gradual applying of a safe controlled tension;

and a means for measuring and displaying the tension in the suture integrally attached to said tension means;

and said smooth suture is a band suture which is flexible for bending along its length and is resistant to bending along its width.

2. A device according to claim 1 wherein the rotating component is a lead screw, a drum, or a helical drive shaft.

3. A device according to claim 1 wherein the means for measuring and displaying the tension in the suture loop is a tension meter, such as a torque meter, a dynamometer, a lever gage, or a tension-meter.

4. A device according to claim 1 wherein in addition said tension means is characterized by having a switching mechanism which allows for relieving any excess suture tension by releasing suture back into the suture loop.

5. A device according to claim 1 wherein the suture head end has an integrally attached surgical needle.

6. A device according to claim 1 wherein the suture tail end has a cross section enlargement or a clip, for facile grasp by the tension means.

7. A device according to claim 1 having in addition a pair of suture supporting skin reinforcing means connected to the skin on both sides of the wound for preventing ripping of the skin when tension is applied to the suture loop, each of said reinforcing means being comprised of a rigid plate for placing on the skin near a suture's skin piercing point wherein the suture passes over or passes through the plate, and a means for preventing said plate from slipping.

8. A device according to claim 7 wherein a reinforcing means is a staple having a broad back for supporting the suture, and having integral skin piercing stickers at both ends for preventing slippage.

9. A device according to claim 7 wherein a reinforcing means is a plate having a broad back for supporting the suture, and having integral skin piercing stickers for preventing slippage.

10. A device according to claim 7 wherein the means for preventing said plate from slipping is by adhesive.

11. A device according to claim 7 wherein a reinforcing means is integrally affixed to the wound facing side of the tension means, for placement against the skin at the suture entry point or at the suture exit point.

12. A device according to claim 1 wherein the suture loop tension means is comprised of a suture ends holder assembly, said assembly having two openings for passing respective suture ends through, a clip located at one of said openings for grasping the first end of the suture, a ratcheted drum (43, 34) located above the other opening (42) for applying wound closing tension through the attached or passing second end of the suture, and means for manually turning said drum (47).

13. A device according to claim 12 wherein a spring (54) is located in said holder and pressing on the ratchet (43) for releasing the ratchet teeth from their counter locking tooth (56) whenever the suture loop tension is exceeding the predetermined spring tension.

14. A device according to claim 1 wherein the suture loop tension means is comprised of a suture ends holder assembly, said assembly having two openings (20, 24) for passing respective suture ends through, a clip (14) located at one of said openings for grasping the first end of the suture, a reversible lead screw (28) located above the other opening (24) for applying or releasing wound closing tension through the passing second end of the suture, and means for manually turning said screw (21).

15. A device according to claim 14 wherein in addition the holder facing end of the screw (29) is ball profiled, and a ball joint socket (30) with an elongated opening located in the holder holds the ball end of the screw, allowing the angle of the screw in the holder to be manually switched to either an open position for the complete release of applied tension to the suture loop, or to a closed position for the complete prevention of any release of excess tension in the suture loop.

16. A device according to claim 1 wherein the first end of the suture is integrally attached to the suture loop tension means.

17. A device according to claim 1 wherein the suture loop tension means is comprised of a rigid casing (90), having;

(a) suture passage openings (105, 109, 120);

(b) a clip (103) located near one of said openings, for invariably grasping one end of the suture;

(c) a helical drive shaft (91) and pinion (92) mechanism, for applying a controlled wound closing tension to the suture loop;

(d) means (94) for manually turning said helical drive shaft clockwise or counterclockwise for driving the suture and controlling its tension;

(e) locking mechanism (96) for locking and unlocking the suture band (100) second end;

wherein in the locking position, the suture loop tension is under the control of the helical drive shaft rotation, and in the unlock position, the suture tension is released, allowing hand pulling the suture through the casing.

18. A device according to claim 17, wherein additionally to a rotational movement, the helical drive shaft is spring (99) loaded for having a path of springy back and forth movement, such that the relative position of the shaft along said path, is determined according to the suture loop tension.

19. A method for closing wounds using a suture tightening wound closure device, comprising sewing a smooth suture across an open wound through the skin and underlying tissue; applying a pair of reinforcing means on skin covered sides of the wound; and, affixing the suture ends in a tension means, and gradually applying a predetermined tension to the suture loop with intervals for skin stress self relaxation until the wound edges are brought into proper alignment, or until the wound is otherwise sufficiently closed, or for delayed primary closure of said wound, wherein the predetermined tension is not exceeding a safe level as measured by a tension meter.

20. A method according to claim 19 comprising the sewing of parallel sutures across an open wound, and applying tension means to each suture independently.

21. A method according to claim 20 comprising supporting more than one suture by a pair of reinforcing means.

* * * * *